(12) United States Patent
Brown

(10) Patent No.: US 7,597,678 B2
(45) Date of Patent: Oct. 6, 2009

(54) APPARATUS AND METHODS FOR ISOLATING LENS CAPSULE FLUIDS

(76) Inventor: David C. Brown, 1195 Caloosa Dr., Fort Myers, FL (US) 33901

( * ) Notice: Subject to any disclaimer, the term of this patent is extended or adjusted under 35 U.S.C. 154(b) by 857 days.

(21) Appl. No.: 10/888,298

(22) Filed: Jul. 9, 2004

(65) Prior Publication Data

US 2006/0009782 A1   Jan. 12, 2006

(51) Int. Cl.
*A61M 27/00* (2006.01)
(52) U.S. Cl. ............... 604/8; 604/541; 623/4.1; 623/6.12; 623/6.38; 623/6.39
(58) Field of Classification Search .......... 604/8; 623/4.1, 6.38, 6.12, 6.39
See application file for complete search history.

(56) References Cited

U.S. PATENT DOCUMENTS

| 3,991,426 | A | * | 11/1976 | Flom et al. ............... 623/6.12 |
| 4,056,855 | A | * | 11/1977 | Kelman ................... 623/6.38 |
| 4,449,257 | A | * | 5/1984 | Koeniger .................. 623/6.39 |
| 5,681,275 | A | | 10/1997 | Ahmed |
| 5,843,184 | A | | 12/1998 | Cionni |
| 6,358,279 | B1 | * | 3/2002 | Tahi et al. .................. 623/4.1 |
| 6,413,277 | B1 | | 7/2002 | Neuhann |
| 6,620,098 | B1 | | 9/2003 | Milverton |
| 2003/0149479 | A1 | | 8/2003 | Snyder et al. |
| 2004/0006387 | A1 | | 1/2004 | Kelman |
| 2004/0010284 | A1 | | 1/2004 | Maloof et al. |

FOREIGN PATENT DOCUMENTS

| WO | WO 03/022191 | 3/2003 |
| WO | WO 2004/017877 | 3/2004 |

* cited by examiner

*Primary Examiner*—Michele Kidwell
*Assistant Examiner*—Ilya Y Treyger
(74) *Attorney, Agent, or Firm*—Claude E. Cooke, Jr.; Burleson Cooke L.L.P.

(57) ABSTRACT

A device to be inserted within a lens capsule during ocular surgery to contain fluids, including therapeutic and optical materials, used for irrigation within the capsule is provided. The device includes a deformable membrane within a ring. One or more ports are provided for irrigation within the capsule. Reduced pressure in an area around the periphery of the membrane may be used for forming a sealing area between the device and the posterior surface of the capsule. Method for inserting the device into the capsule and performing irrigation or aspiration for polishing and for deforming the lens capsule is provided. The device may be placed in an eye for permanent isolation of fluids within the lens capsule from tissue and fluids outside the capsule.

22 Claims, 5 Drawing Sheets

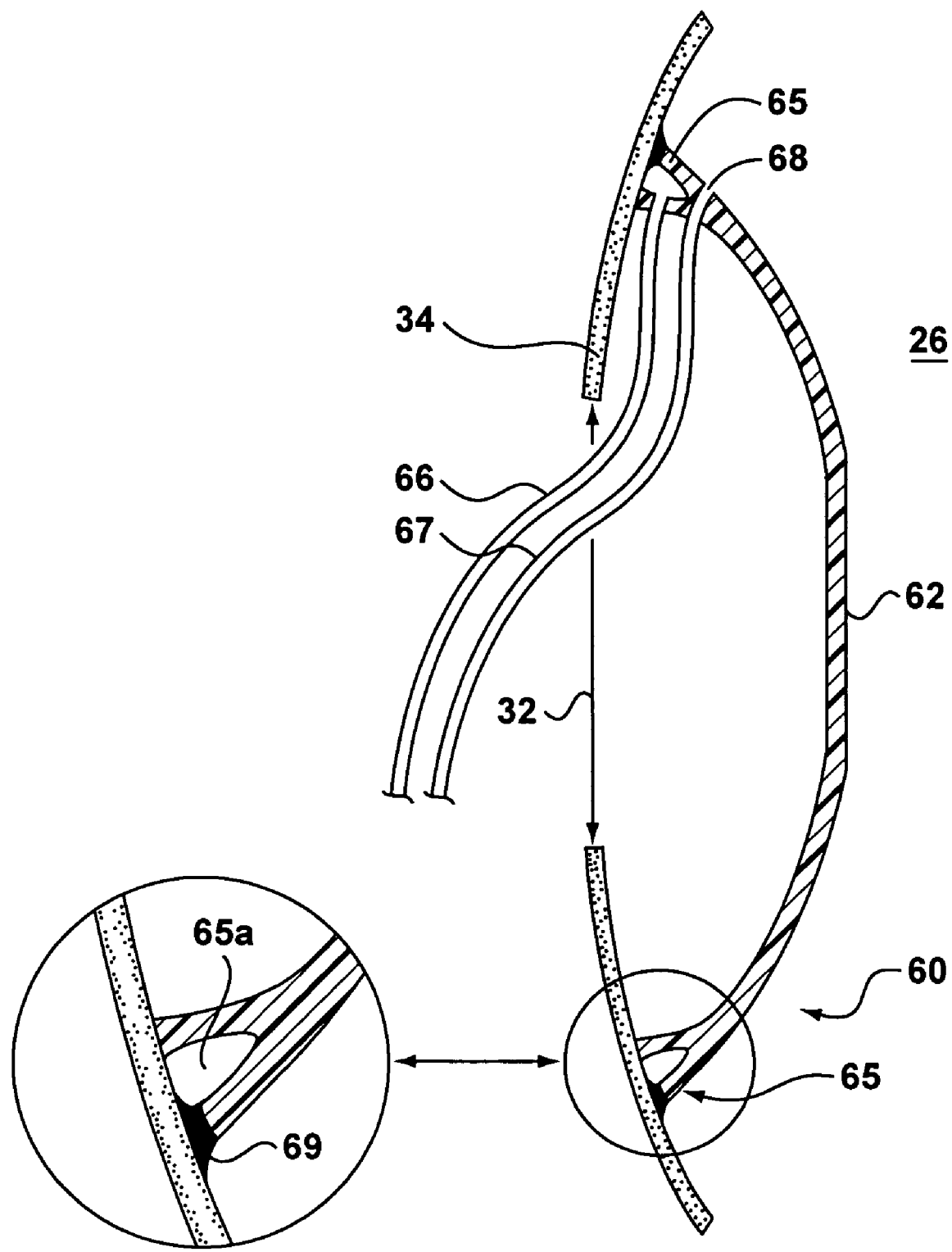
*Figure 4A* *Figure 4*

APPARATUS AND METHODS FOR ISOLATING LENS CAPSULE FLUIDS

BACKGROUND OF THE INVENTION

1. Field of the Invention

This invention pertains to apparatus and method for isolating fluids within the lens capsule in an eye from extracapsular tissues and intraocular fluids. More particularly, a sealing device adapted for placing inside a lens capsule and method for using the device are provided.

2. Description of Related Art

After removal of the human lens contents in ocular surgery, normal surgical procedure includes irrigation of the lens capsule to remove lens epithelial cells and lens fibers or cortex before implanting an intraocular lens (IOL). This procedure is called "polishing" the capsule. If all lens epithelial cells are not removed, they may cause posterior capsule opacification (PCO). PCO is the most common complication of cataract surgery and is a widespread cause of vision loss. Improved procedures for polishing the lens capsule before implanting an IOL are needed. There is a need to isolate the fluid used for capsule polishing (water or an aqueous solution of a chemical agent) from the exterior of the capsule. In other words, fluid communication from the interior to the exterior of the capsule should be eliminated, so that the tissues or intraocular fluids in the eye will not be affected by the polishing procedure. Effective and complete fluid isolation can make possible the use of even more effective polishing solutions. Techniques are being considered and may be developed in the future that depend even more critically on a complete removal from the interior of the capsule of any cells that may cause fibrosis or PCO.

Consideration is also being given to surgical techniques to improve vision in a phakic eye by techniques other than implantation of an IOL in the lens capsule. Some of these techniques involve reshaping or refilling the lens capsule for anatomical or optical (refractive) objectives by introducing liquids or gels into the lens capsule. For example, fluids may be developed for placement in a lens capsule to maintain elasticity of the capsule. Other fluids or materials may be developed to replace the natural lens contents with a material having a selected refractive index. In these cases, also, there is need to isolate the capsule from extracapsular tissues and intraocular fluids. Some of these techniques may also need a permanent membrane (artificial anterior capsule) to seal a capsulorhexis. Other surgical techniques that may benefit from apparatus and method for isolating fluid inside a capsule include: obtaining volumetric measurements of the intracapsular volume; expanding or reforming the capsular bag to aid in lens implantation, lens reposition or lens exchange; and removing secondary cataract pearls, fibrotic material or debris from the capsule, with or without lens implantation.

Recently the "Perfect Capsule™" device has become available for use during cataract surgery. Such device is disclosed in Pub. No. US2004/0010284 A1. This is a single use sterile capsule holding and sealing device used for irrigation of the capsular bag. The device includes a "vacuum" ring that may be activated by a vacuum syringe. The vacuum ring is oriented to seal against the anterior surface of the lens capsule. One or two ports in the device allow an irrigating solution to be injected or removed without contacting other internal structures of the eye after a seal between the device and the anterior surface is established. In one embodiment, the device includes a flexible "plug" that can be inserted through the incision and placed onto the exterior of the anterior surface of the capsule and around the capsulorhexis. In one embodiment, one tube is for aspiration of fluid and is attached to an aspiration port and a second tube communicates with a second port in the surface of the plug. The second tube and port may be omitted if irrigation and aspiration steps are performed sequentially. The device is molded from materials such as silicone or polyurethane such that it can be rolled into a form allowing it to pass through the normal incision into the anterior chamber of the eye.

While the Perfect Capsule™ affords a method to allow irrigation of the lens capsule without affecting other portions of an eye, there is a need for a sealing device and method to allow easier placement of the device during surgery. The device should allow observation of position and ready manipulation of position with respect to the capsulorhexis. Also, there is a need for a sealing device that can be used in other procedures to isolate fluids inside a lens capsule from tissues and fluids outside the capsule, either during surgery or for permanent placement.

SUMMARY OF THE INVENTION

A device to isolate fluids within a lens capsule from other parts of an eye is provided. The device is placed within the capsule and forms a sealing area with the posterior surface of the anterior capsule. The device includes a ring that forms the sealing area; the ring encloses a membrane. A tube can be used to reduce pressure in the ring to form the sealing area. A port opening into the lens capsule via the device may allow fluid to be used for irrigation within the capsule while confining the fluid to the capsule. More than one port into the lens capsule via the device may be used. The device is placed within a lens capsule and reduced pressure may be applied to the tube to form the sealing surface with a "vacuum" (reduced pressure) ring. Fluid may then be aspirated or used for irrigation by flow through a port opening through the device into the lens capsule before the device is removed from the eye. Other fluids or materials may be introduced into the lens capsule for a variety of purposes before the device is removed from the eye. In another embodiment, the device is permanently affixed to the capsule and serves to isolate fluids or materials within the capsule, creating an artificial anterior capsule.

BRIEF DESCRIPTION OF THE DRAWINGS

FIG. 4 is a cross-section view of another embodiment of the device having a tube into the flow channel and one port through the ring.

The same numeral in different figures denotes the same part of an eye.

DETAILED DESCRIPTION

Figure 1:
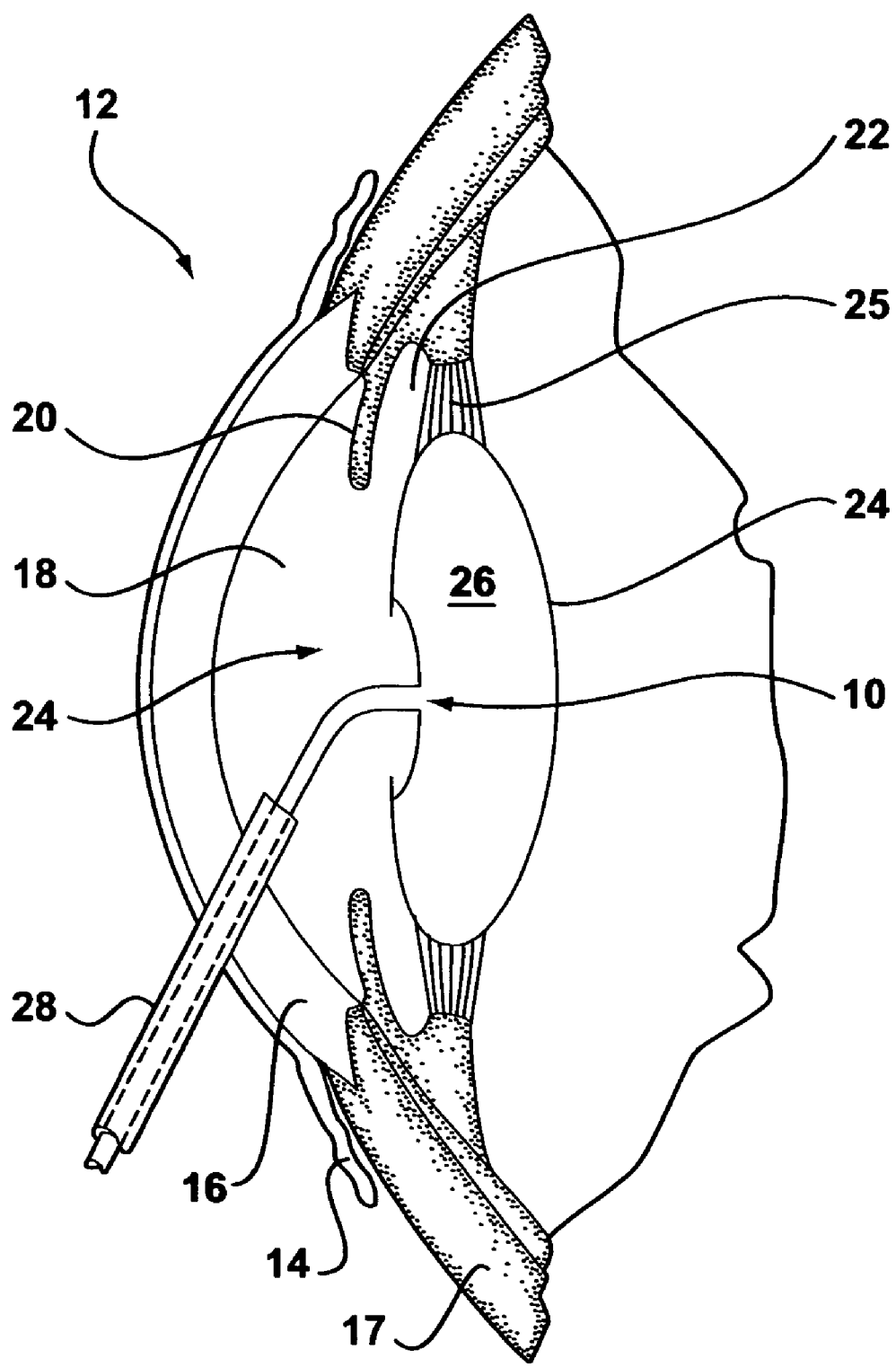
FIG. 1 illustrates an eye in cross-section with a device disposed within the lens capsule of the eye and an insertion device or injector entering the eye.

FIG. 1 shows device 10 deployed within lens capsule 24 of eye 12. Device 10 may be placed through an incision in conjunctiva 14 and cornea 16 (or through clear cornea 16 if conjunctiva 14 is not present) or through sclera 17 into anterior chamber 18, through iris 20 and posterior chamber 22 and through a surgical opening (capsulorhexis) in lens capsule 24. Lens capsule 24 is attached to and affected by lens zonules 25. The interior of the lens capsule is shown at 26. Insertion support or injector 28 may be used for insertion of device 10.

Figures 2, 2A:
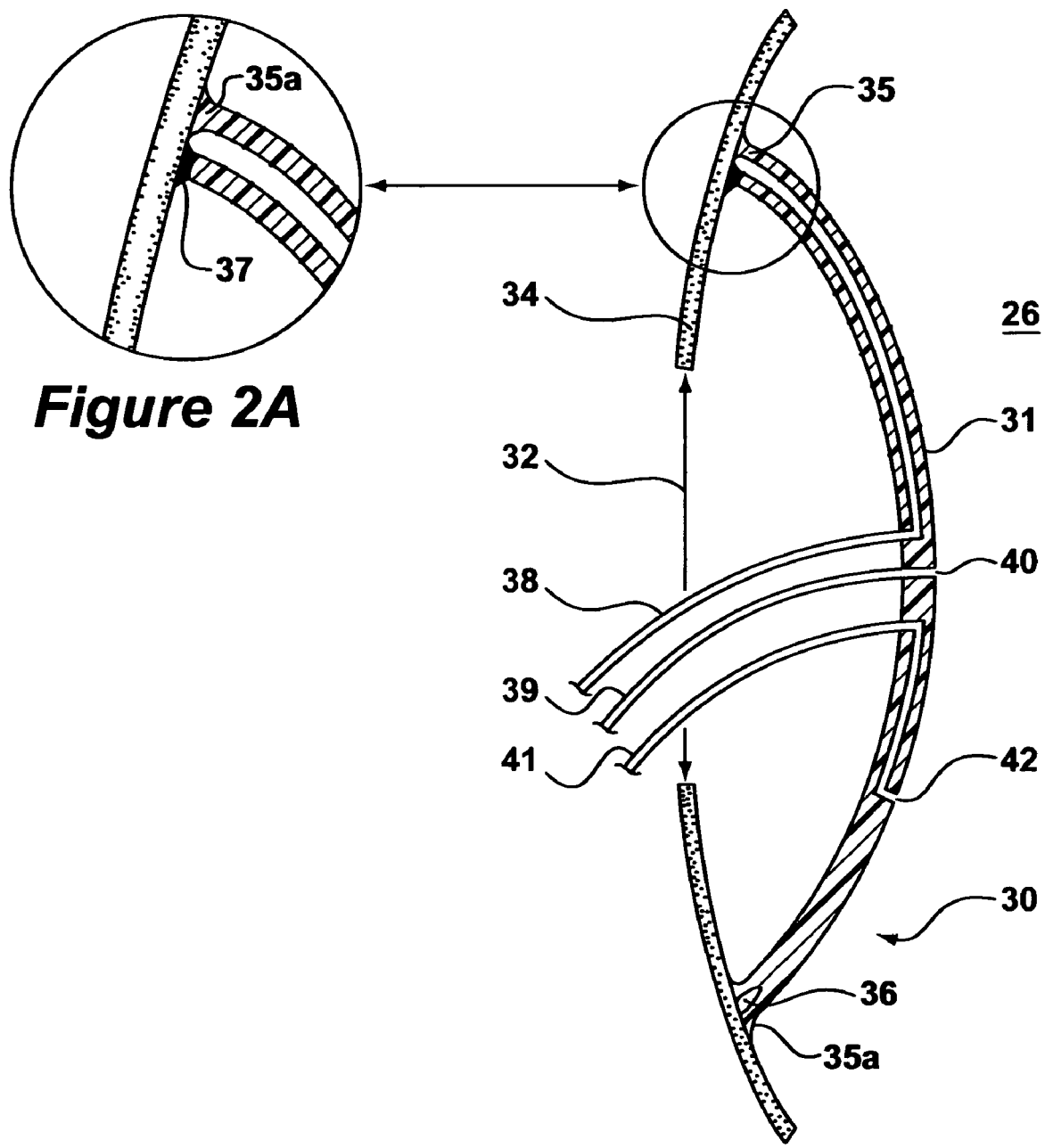
FIG. 2 is a cross-section view of one embodiment of the device where flow channels through the membrane provide flow communication from the ring at the periphery of the membrane to a tube and the membrane includes two ports.

Referring to FIG. 2, one embodiment of device 10 of FIG. 1 is shown at 30, disposed in interior 26 of the lens capsule of an eye. Device 30 has been inserted through capsulorhexis (surgical opening) 32 and is held to the posterior (or inner) surface 34 of the anterior capsule by circumferential ring 35, which includes flow channel 36 and a pair of sealing lips 35a (inset FIG. 2A), which form a sealing area around the periphery of membrane 31. A "ring" as used herein is the peripheral segment of the device, normally having greater wall thickness than the "membrane," which it encloses. Sealing lips 35a are oriented and positioned so as to come into proximity to surface 34 after device 30 is inserted and positioned through capsulorhexis 32. Therefore, device 30 is adapted to form a sealing surface from within a lens capsule. Flow channel 36 is in flow communication with tube 38. A selected reduced pressure can be applied to flow channel 36 through tube 38 to cause device 30 to be held in place and sealed (form a sealing area) between the posterior surface of anterior capsule 34 and sealing lips 35a of ring 35. A cannula may be used without the necessity of a tube in some cases. Either can be considered a "conduit" for purposes of this disclosure. Colorant 37 may be placed in device 30 in the vicinity of or within ring 35. Such colorant may be used by the surgeon in placing or locating ring 35 of device 30 around capsulorhexis 32. The colorant may be black or colored particles, for example, molded or otherwise placed into the material of the device. Ring 35 may include an increased cross-sectional area of sealing lips 35a where they contact posterior surface 34 to allow less stress per unit area when device 30 is sealed to surface 34, as illustrated in inset FIG. 2A. A soft deformable elastomer may be used in at least the distal end of sealing lips 35a to allow greater distribution of stress and to increase sealing area. Tubes 39 and 41 are in flow communication with ports 40 and 42, respectively, in membrane 31 to allow aspiration or irrigation in interior 26 of the capsule. Ports 40 and 42 open in the posterior surface of membrane 31 and within the lens capsule. Membrane 31 of device 30 may be flat or other shapes and may deform from its original shape during insertion and when aspiration or irrigation is being applied. The ports may be disposed so as to afford more effective aspiration or irrigation within capsule interior 26. Either port 40 or 42 may be omitted if it is desired to practice irrigation and aspiration through the same tube. Alternatively, either tube 38 or tube 39 may not be used, allowing fluid to drain from either port into the eye. Device 30 may be molded from a non-biodegradable material such as an elastomer or polymer such as silicone or other flexible material that can be used in a human body. Such materials are well known. The material should be deformable to allow the device to be folded or rolled into a dimension allowing it to pass through a normal incision used in the lens surgery. Forceps or other insertion devices known in the art may be used to assist in placing the device through the incision and capsulorhexis 32, or the device may be placed using insertion support or injector 28, shown in FIG. 1.

Figures 3, 3A:
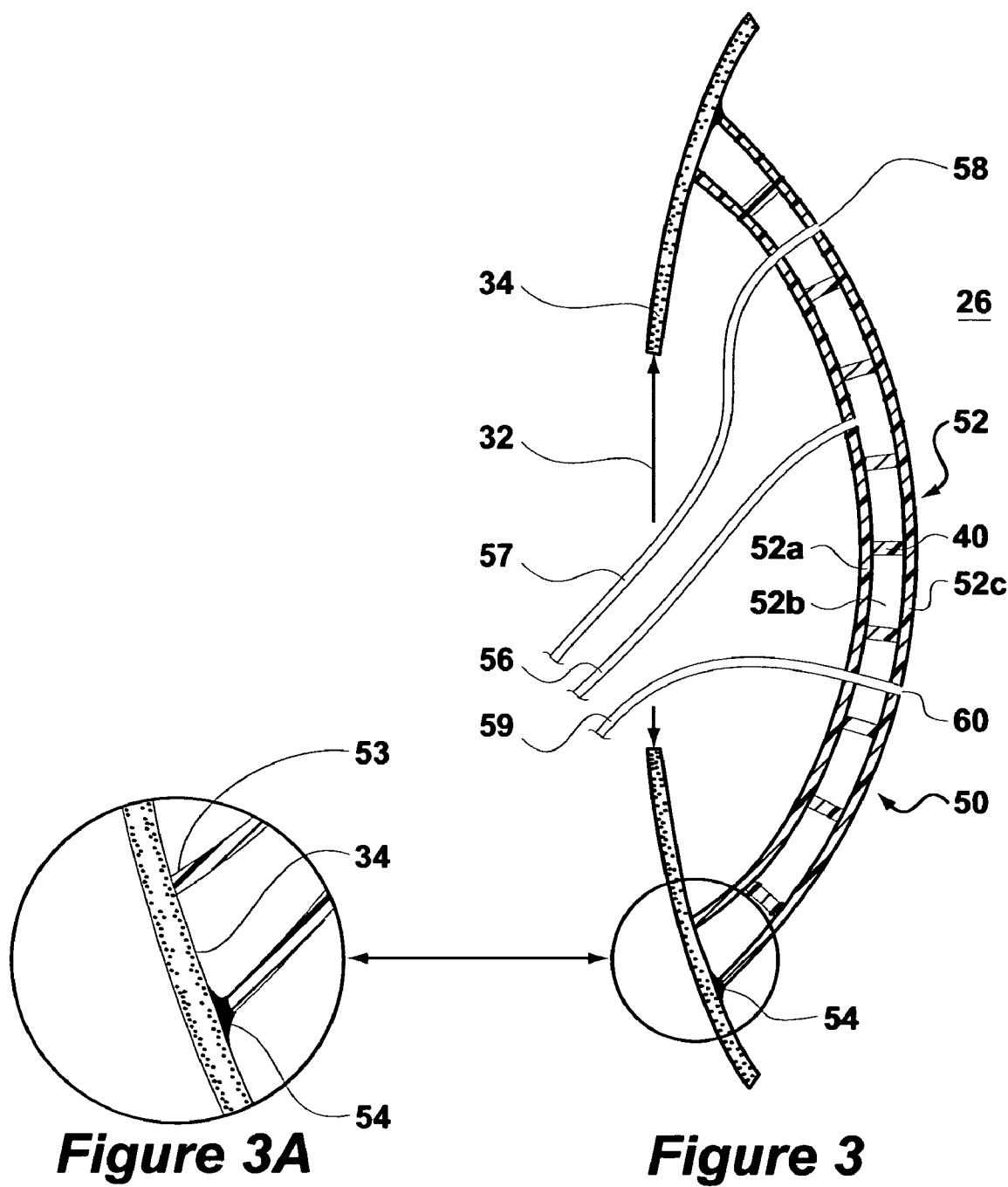
FIG. 3 is a cross-section view of another embodiment of the device where a fluid-permeable zone between the skins of the membrane provides flow communication from the ring at the periphery of the membrane to a tube.

Referring to FIG. 3, a second embodiment of device 10 of FIG. 1 is shown at 50. Membrane 52 of the device includes inner skin 52a, outer skin 52c and fluid-permeable region 52b between the skins. Region 52b supports the separation of the membranes when a decreased pressure is applied between the membranes. It may be formed of ribs (as shown), open cell foam, particles of deformable material, or any other structure affording permeability to fluid flow along and between the skins. On the periphery of membrane 52, skins 52a and 52c may be enlarged in cross-sectional area, so as to afford greater sealing surface area or sealing lips, as at 54 (inset FIG. 3A), against the posterior surface of anterior capsule 34. The sealing area of the skins and the fluid-permeable region 52b between the skins form a "ring" on the periphery of membrane 52, and a sealing area can be formed between the ring and the posterior surface of anterior capsule 34 by reducing fluid pressure in tube 56. Sealing lips as at 53 and 54 (FIG. 3A) are oriented and positioned so as to come into proximity to surface 34 after device 50 is inserted through capsulorhexis 32 and positioned. Therefore, device 50 is adapted to form a sealing area from within the capsule. Colorant 54 may be added to one or both of the skins on the periphery to provide the surgeon greater ability to observe the position of device 50 covering and sealing around capsulorhexis 32. Tube 56 is connected to region 52c so that reduced fluid pressure can be attained within region 52c, allowing the ring at the periphery of membrane 52 to seal against the posterior surface of anterior capsule 34, or form a sealing area.

Ports 58 and 60, connected with tubes 57 and 59, respectively, may be used for irrigation and aspiration of interior 26 of a capsule. The ports may be disposed in any location along membrane 52 or in ring 53. Either port 58 or 60 may be omitted if it is desired to practice irrigation and aspiration through the same tube. Device 50 may be molded from an elastomer or polymer such as silicone or other flexible material that can be used in a human body. The material may be deformable to allow it to be folded or rolled into a dimension allowing it to pass through a normal incision used in lens surgery. Although membrane 52 it shown as having a dome shape, it should be understood that the membrane may be flat and also may be deformed from its original shape when aspiration or irrigation is in progress. Forceps or other insertion devices known in the art may be used to assist in placing the device through the incision and opening 32, or the device may be placed using support or injector 28, shown in FIG. 1.

FIG. 4 illustrates another embodiment of the device. Device 60 has been placed through capsulorhexis 32 into volume 26 of a lens capsule in the eye. Membrane 62 extends between ring 65, including flow channel 65a (FIG. 4A). Tube 66 is in flow communication with channel 65a and tube 67 extends through ring 65 and is flow-connected to port 68. Sealing lips around flow channel 65a are oriented and positioned so as to come into proximity to the posterior surface of anterior capsule 34 after device 50 is inserted through capsulorhexis 32 and positioned. Therefore, device 50 is adapted to form a sealing area from within the lens capsule. The sealing area is formed by reducing fluid pressure in tube 66 and flow channel 65a.

Inset FIG. 4A shows colorant 69 that may be placed in a sealing lip of ring 65, as discussed previously. Membrane 62 is flexible and may have a shape dependent on placement in the eye and flow conditions through tubes 66 and 67.

The diameter of the membrane of devices shown in FIG. 2, FIG. 3 and FIG. 4, when deployed within a capsule is adapted to seal against the posterior surface of the anterior capsule and around the capsulorhexis. Generally, a diameter in the range of about 4 mm to about 8 mm may be used. The inside diameter of tubes is adapted to pass fluid at a desired rate and to fit -within space limitations imposed by passing through an incision and capsulorhexis. Generally, tubes for aspiration and irrigation may have an internal diameter in the range of about 0.2 to about 0.4 mm. Wall thickness of tubes will be designed to allow positive and negative pressures in a desired operating range. Total outside diameter of all tubes will be kept within a value to allow separate tubes to be bundled together or made into an integral tube having a size to pass through an incision, which is generally in the range of about 3 mm in the largest dimension, and a capsulorhexis, which may be from 1 to 7 mm or more in diameter. A handle to be used in placing or positioning the devices can be in the form of a rod used alongside a tube or separately or a conduit used as a tube and having enough stiffness to support the device.

The devices of FIG. 2, FIG. 3 and FIG. 4 may be deployed within a capsule using forceps and normal surgical procedures. Alternatively, the devices may be deployed by use of a insertion support or injector, such as shown at 28 in FIG. 1. Such devices for inserting devices in an eye are well known in the art. The devices of FIG. 2, FIG. 3 and FIG. 4 may be made of elastomers or other polymers and may be folded or wrapped to be contained in injector 28. When the end of support 28 has passed through capsulorhexis 32, the device may be forced from support 28, allowing the membrane and ring to unfold within the capsule. The device is then positioned to insure that the periphery of the device contacts the posterior surface of the anterior capsule. The membrane or the ring may be colored to aid in visualization of placement. In positioning the ring, air, liquid or a gel material may be injected through the irrigation/aspiration tube to assist in positioning the suction ring on the posterior surface 34 of the anterior capsule. The gaseous, liquid or gel material may be injected to assist in floating the membrane and ring into position.

After the device is in place within the capsule and under the capsulorhexis, pressure may be reduced at the ring by applying a reduced pressure (below intraocular pressure) to the tube in flow communication with the channel at the periphery of the device (FIGS. 2 and 4) or between the skins of the device (FIG. 3). The reduced pressure is necessary to bring the membrane in close contact with the posterior surface of the anterior capsule and form a sealing area. Since force on the membrane is in the direction of posterior surface 34 as pressure is applied to the capsule during irrigation, the ring will be forced into closer contact with the posterior surface during irrigation of the capsule. In the embodiment of the device having two ports in the membrane or ring, as liquid is infused in the liquid may be allowed to flow out of the eye. In any case, a significant increase in intracapsular pressure is not expected during use of the devices disclosed.

The disclosed device may be used during normal surgical procedures with addition of the steps of placing the device in a lens capsule after phacoemulsification or other procedures to empty the capsule or replace original material in the capsule are complete. The device is positioned such that the ring or periphery of the membrane is below the capsulorhexis and is in contact with the inside surface of the capsule (the posterior surface of the anterior capsule). Pressure is reduced in the ring to bring the ring in sealing contact with the inside or posterior surface of the capsule. Fluid is then introduced and removed from the capsule through one or two ports in the membrane or ring. The fluid may be selected to destroy cells remaining in the capsule. The device is then removed from the eye.

The disclosed device may also be used in conjunction with other surgical procedures. The device may be used to obtain volumetric measurements of the intracapsular volume. After the device is in place and the sealing area is formed, the volume of fluid used in filling the capsule after aspiration of its contents or the volume of fluid extracted during aspiration may be measured directly. The device may be used to expand or reform the capsular bag to aid in lens implantation, repositioning or lens exchange. The device may be used to aid in removal of secondary cataract pearls, fibrotic material of debris from the capsule, whether or not lens implantation follows. In each of these applications, the device is placed within the capsule and the sealing area between the device and the posterior surface of the anterior capsule is formed as described heretofore. The surgical procedure is then performed.

Figures 5, 5A:
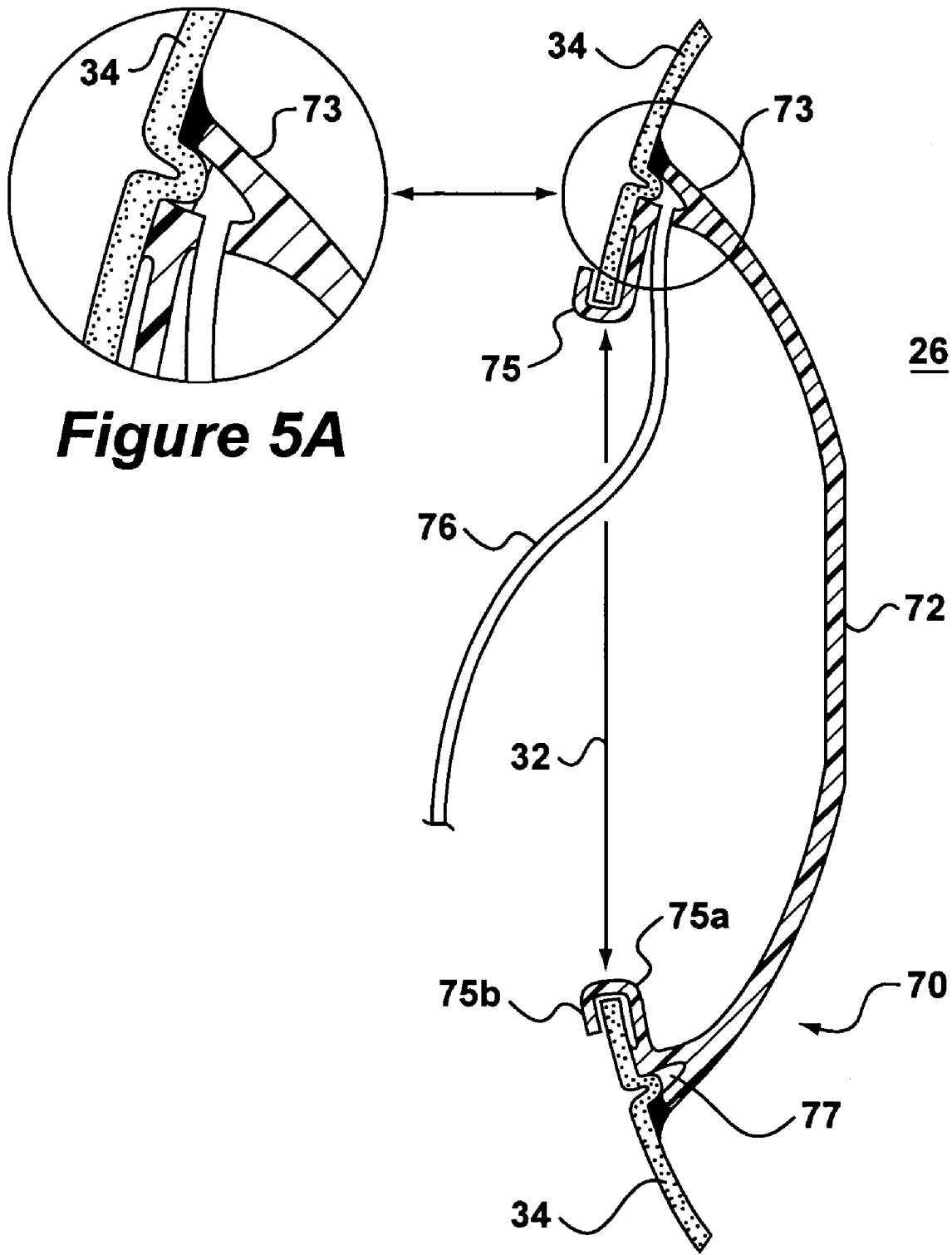
FIG. 5 is a cross-section view of another embodiment of the device having a collar for affixing the device to an anterior capsule and providing for reduced pressure to pinch and hold the anterior capsule.

In other embodiments, the device disclosed heretofore is modified to be adapted for permanent placement in an eye. Such permanent placement may be used to shape or expand the capsule and maintain such shape when implantable materials are utilized, for example. Another application of a permanent barrier or seal of the capsular bag would be after injection of refractive fluids or materials to replace the lens content, or solutions to maintain elasticity of the capsule or after placement of other physiological or optical materials or devices in the capsule. For these applications, the device illustrated in FIG. 5 may be used. The device having a ring and membrane as described above is modified to be affixed permanently to the anterior capsule. The device may include a port that would connect inside and outside the capsule after the device is placed in an eye or it may not contain a port and not be used for irrigation or aspiration of the capsule. If a port is present, the port is preferably plugged before the device is placed in an eye. (A plugged port is not shown in FIG. 5.) Two methods of affixation are illustrated, using modifications to the device of FIG. 4. It should be understood that similar modifications could be made to the devices of FIG. 2 or FIG. 3 or any other device having a ring to form a seal area and a membrane. Preferably the membrane will have maximum optical clarity and transmission. Referring to FIG. 5, device 70 is illustrated. Collar 75 is formed extending from ring 73. Collar 75 is adapted to receive the segment of anterior capsule 34 between ring 73 and capsulorhexis 32, to be placed between legs 75a and 75b of the collar. In one embodiment, collar 75 serves as a barrier to flow or mixing of fluids from interior 26 of the capsule, but a seal is not formed. In another embodiment, a tissue adhesive, which is known in the art, is placed on collar 75 or on the interior surfaces of legs 75a and 75b of 75, either before or after it is placed in the eye. In this embodiment, a permanent seal of the capsule is attained.

Still referring to FIG. 5, an alternative permanent sealing mechanism is illustrated. Device 70 has been placed in an eye. A segment of anterior capsule 34 in the form of a ring is shown folded to enter a portion of flow channel 77 within ring 73. Ring 73 is constructed to receive the segment of anterior capsule 34 in contact with ring 73 when a sufficiently reduced pressure is applied to the sealing area between ring 73 and the posterior surface of anterior capsule 34. The reduced pressure in flow channel 77 pulls anterior capsule 34 into flow channel 77. Further, ring 73 is constructed to pinch anterior capsule 34 with sufficient force to keep the segment of anterior capsule in place within ring 73 and form a permanent seal of device 70 to anterior capsule 34, thus sealing and isolating volume 26 of the capsule. This pinching arrangement may be supplied by elasticity properties in ring 73 or by other mechanical spring force applied radially in ring 73. A ridge running along within flow channel 77 may be used to decrease the width of flow channel 77 before it is intersected by tube 76, so as to keep flow channel 77 open throughout ring 73. Alternatively, a perforated partition may be placed in flow channel 77 so as to limit movement of a ring of anterior capsule 34 into flow channel 77. These embodiments are illustrated in FIG. 5A by short lines extending into flow channel 77 and contacting anterior capsule 34. If port 68 (FIG. 4) is present, it may be plugged to complete isolation of fluid within capsule volume 26.

Although the present invention has been described with reference to specific details, it is not intended that such details should be regarded as limitations on the scope of the invention, except as and to the extent that they are included in the accompanying claims.

What I claim is:

1. A device to isolate fluids within a lens capsule of an eye during a surgical procedure, the lens capsule having an anterior capsule, the anterior capsule having a posterior surface, comprising:
    a ring and a membrane therewithin, the ring being adapted to form a sealing area on the posterior surface from within the capsule, the sealing area being in fluid communication with a first conduit extending outside the capsule; and
    a first port in the ring or the membrane, the first port allowing fluid communication from outside the capsule to within the capsule when the sealing area on the posterior surface is formed.

2. The device of claim 1 further comprising a second conduit in fluid communication with the first port.

3. The device of claim 1 further comprising a second port, the second port allowing fluid communication from outside the capsule to within the capsule when the sealing area is formed.

4. The device of claim 1 wherein the ring and membrane are formed from a material selected to be used in a human body.

5. The device of claim 1 wherein the sealing area is in flow communication with the first conduit through a single flow channel in the membrane or the ring.

6. The device of claim 1 wherein the sealing area is in flow communication with the first conduit through a fluid-permeable region between a pair of skins forming the membrane.

7. The device of claim 1 further comprising a colorant in the ring.

8. The device of claim 1 further comprising an injector, the injector being adapted to confine the ring and membrane during placement in an eye.

9. A method for irrigating or aspirating fluid within a lens capsule of an eye, comprising:
    forming an incision and a capsulorhexis in the anterior capsule of the eye, the anterior capsule having a posterior surface;
    placing within the lens capsule a device having a ring and a membrane therewithin, the ring being adapted to form a sealing area on the posterior surface from within the capsule, the sealing area being in fluid communication with a first conduit extending outside the capsule, and a first port in the ring or the membrane, the first port allowing fluid communication from outside the capsule to within the capsule;
    positioning the ring around the capsulorhexis and inside the lens capsule;
    applying a reduced pressure to the first conduit so as to form the sealing area;
    irrigating or aspirating fluid through the first port; and
    removing the device from the eye.

10. The method of claim 9 wherein the ring and membrane are confined and placed within the lens capsule by use of forceps.

11. The method of claim 9 wherein the ring and membrane are confined and placed within the lens capsule by use of an injector.

12. The method of claim 9 wherein the ring further comprises a colorant and the positioning includes observing the location of the colorant with respect to the capsulorhexis.

13. The method of claim 9 wherein the device further comprises a second port in the ring or the membrane, the second port allowing fluid communication from outside the capsule to within the capsule, further comprising irrigating or aspirating fluid through the second port.

14. A method for placing a fluid within a lens capsule of an eye, comprising:
    forming an incision and a capsulorhexis in the anterior capsule of the eye, the anterior capsule having a posterior surface;
    placing within the lens capsule a device having a ring and a membrane therewithin, the ring being adapted to form a sealing area on the posterior surface from within the capsule, the sealing area being in fluid communication with a first conduit extending outside the capsule, and a first port in the ring or the membrane, the first port allowing fluid communication from outside the capsule to within the capsule;
    positioning the ring around the capsulorhexis and inside the capsule;
    applying a reduced pressure to the first conduit so as to form the sealing area;
    injecting the fluid through the first port into the capsule; and
    removing the device from the eye.

15. The method of claim 14 further comprising measuring the volume of the capsule before the step of removing the device from the eye.

16. The method of claim 14 wherein the fluid injected through the first port into the capsule is a fluid or gel material and further comprising lens implantation, lens reposition or lens exchange before the step of removing the device from the eye.

17. The method of claim 14 further comprising removal of secondary cataract pearls, fibrotic material or debris from the capsule before the step of removing the device from the eye.

18. A device to isolate fluids within a lens capsule of an eye, the lens capsule having an anterior capsule, the anterior capsule having a posterior surface, comprising:
    a ring and a membrane therewithin, the ring being adapted to form a sealing area on the posterior surface from within the capsule, the sealing area being adapted for fluid communication with a first conduit that is adapted to extend outside the capsule; and
    a collar extending from the ring so as to receive a segment of the anterior capsule.

19. The device of claim 18 further comprising a colorant in the ring.

20. The device of claim 18 further comprising a tissue adhesive on the collar.

21. A device to isolate fluids within a lens capsule of an eye, the leans capsule having an anterior capsule, the anterior capsule having a posterior surface, comprising:
    a ring and a membrane therewithin, the ring being adapted to form a sealing area on the posterior surface from within the capsule, the sealing area being adapted for fluid communication with a first conduit extending outside the capsule; and
    a pinching arrangement in the ring to retain the anterior capsule within the ring after the sealing area is formed.

22. The device of claim 21 further comprising a colorant in the ring.

* * * * *